(12) United States Patent
Jiang

(10) Patent No.: US 7,767,720 B2
(45) Date of Patent: Aug. 3, 2010

(54) LARGE-SCALE COLLOIDAL CRYSTALS AND MACROPOROUS POLYMERS AND METHOD FOR PRODUCING

(75) Inventor: Peng Jiang, Plainsboro, NJ (US)

(73) Assignee: Corning Incorporated, Corning, NY (US)

(*) Notice: Subject to any disclaimer, the term of this patent is extended or adjusted under 35 U.S.C. 154(b) by 596 days.

(21) Appl. No.: 10/980,126

(22) Filed: Nov. 1, 2004

(65) Prior Publication Data
US 2005/0095417 A1    May 5, 2005

Related U.S. Application Data

(60) Provisional application No. 60/516,218, filed on Oct. 31, 2003.

(51) Int. Cl.
C01B 33/14    (2006.01)
B01F 3/12    (2006.01)

(52) U.S. Cl. .............. 516/34; 516/9; 516/31; 516/33

(58) Field of Classification Search .............. 516/9, 516/31, 33, 34
See application file for complete search history.

(56) References Cited

U.S. PATENT DOCUMENTS

| 5,580,819 | A | * | 12/1996 | Li et al. ............... 427/167 |
| 5,944,994 | A | | 8/1999 | Asher et al. ........... 210/500.22 |
| 6,123,845 | A | | 9/2000 | Asher et al. ........... 210/500.22 |
| 6,274,288 | B1 | | 8/2001 | Kewitsch et al. ...... 430/270.14 |
| 2002/0045030 | A1 | * | 4/2002 | Ozin et al. ............ 428/173 |
| 2002/0062782 | A1 | | 5/2002 | Norris et al. .......... 117/3 |
| 2003/0129501 | A1 | | 7/2003 | Megens et al. ........ 430/1 |

FOREIGN PATENT DOCUMENTS

| EP | 1028328 | 8/2000 |
| EP | 1052312 | 11/2000 |
| WO | WO02/33461 | 4/2002 |

OTHER PUBLICATIONS

Weisstein, Eric W., "Hexagonal Close Packing." From MathWorld-A Wolfram Web Resource, http://www.mathworld.wolfram.com/HexagonalClosePacking.html, Copyright 1999-2008, Retrieved Dec. 5, 2008.*
Weisstein, Eric W., "Cubic Close Packing." From MathWorld-A Wolfram Web Resource, http://www.mathworld.wolfram.com/Cubic-ClosePacking.html, Copyright 1999-2008, Retrieved Dec. 5, 2008.*
Jiang, et al.; "Single-Crystal Colloidal Multilayers of Controlled Thickness"; Chem. Mater.; 1999; Issue 11, pp. 2132-2140.
Qian, et al.; Three-Dimensionally Ordered Macroporous Polymer Materials: An Approach for Biosensor Applications; Langmuir; 2002; Issue 18, pp. 4526-4529.
Sun, et al.; Monodisperse FePt Nanoparticles and Ferromagnetic FePt Nanocrystal Superlattices; Science; vol. 287, pp. 1989-1992; Mar. 17, 2000.
Jiang, et al.; "A Lost-Wax Approach to Monodisperse Colloids and Their Crystals"; Science; vol. 291, pp. 453-457; Jan. 19, 2001.
Nykypanchuk, et al.; "Brownian Motion of DNA Confined Within a Two-Dimensional Array"; Science; vol. 297, pp. 987-990; Aug. 9, 2002.
Wijnhoven, et al.; "Preparation of Photonic Crystals Made of Air Spheres in Titania"; Science; vol. 281, pp. 802-804; Aug. 7, 1998.
Liu, et al.; "Entropic Trapping of Macromolecules by Mesoscopic Periodic Voids in a Polymer Hydrogel"; Nature; vol. 397, pp. 141-144; Jan. 14, 1999.
Xia, et al.; "Monodispersed Colloidal Spheres: Old Materials with New Applications"; Adv. Mater.; Issue 12, No. 10; pp. 693-713; 2000.
Vlasov, et al.; "On-chip Natural Assembly of Silicon Photonic Bandgap Crystals"; Nature, vol. 414, pp. 289-293; Nov. 15, 2001.
Holtz, et al; "Polymerized Colloidal Crystal Hydrogel Films as Intelligent Chemical Sensing Materials"; Nature, vol. 389, pp. 829-832; Oct. 23, 1997.
Blanco, et al.; "Large-Scale Synthesis of a Silicon Photonic Crystal with a Complete Three-Dimensional Bandgap near 1.5 Micrometres"; Nature, vol. 405, pp. 437-440; May 25, 2000.
Kraemer, et al.; "Ultra High-Density Optical Data Storage: Information Retrieval an Order of Magnitude Beyond the Rayleigh Limit"; Chemical Physics; vol. 285, pp. 73-83; 2002.
Kamenetzky, et al.; "Structure of Solidified Colloidal Array Laser Filters Studied by Cryogenic Transmission Electron Microscopy"; Science; vol. 263, pp. 207-210; Jan. 14, 1994.
Ozin, et al.; "The Race for the Photonic Chip: Colloidal Crystal Assembly in Silicon Wafers"; Advanced Functional Materials; 11, No. 2, Apr. 2001; pp. 95-104.
Das, et al.; "Study of Refractive Index and Physical Thickness of Porous Silica Films with Ageing in Hydrated Ammonia and Air"; Materials Letters; 57, 2003; pp. 2320-2325.

* cited by examiner

Primary Examiner—Timothy J. Kugel
(74) Attorney, Agent, or Firm—Gregory V. Bean

(57) ABSTRACT

Single domain wafer-scale colloidal crystals and macroporous polymers are formed by dispersing concentrated solutions of colloids, desirably mondisperse silica colloids, in a viscous monomer, desirably ethoxylated trimethylolpropane triacrylate, and spin-coating them onto a substrate. Subsequent photopolymerization produces three-dimensionally ordered colloidal crystals trapped inside a polymer matrix. Selective removal of the polymer matrix, such as by oxygen plasma treatment, or removal of the silica spheres, such as by wet etching, produces large-area colloidal crystals and macroporous polymers, respectively.

4 Claims, 15 Drawing Sheets

10 µm

1 μm

10 μm

5 µm

5 μm

1 μm

2 μm

1 μm

5 μm

10 µm

5 µm

LARGE-SCALE COLLOIDAL CRYSTALS AND MACROPOROUS POLYMERS AND METHOD FOR PRODUCING

This application claims the benefit of priority under 35 U.S.C. §119(e) of U.S. Provisional Application Ser. No. 60/516,218 filed on Oct. 31, 2003.

FIELD OF INVENTION

The present invention relates to large-scale colloidal crystals and to macroporous polymers useful in various applications, including optics and optical devices, microfiltration, and others, and to methods for synthesizing such crystals and polymers. More particularly, the present invention relates particularly to large-scale (as large as six-inch diameter or more) colloidal crystals and macroporous polymers produced through a simple and fast (less than ten-minute) spin coating process, and to said process, and to colloidal crystals and macroporous polymers in which colloid spacing or pore spacing, within a layer of the structure, respectively, is around 1.4 D, where D is the diameter of the colloids or pores.

BACKGROUND

Colloidal crystals (3D periodic structures formed from monodisperse colloids) have been extensively explored due to their important usefulness in applications such as diffractive optical devices chemical and bio-sensors and high-density magnetic data recording materials. Recently they have attracted renewed interest, mainly because they provide a much simpler, faster and cheaper approach than complex semiconductor nanolithography techniques to create 3D photonic crystals working in the optical wavelength range.

Spontaneously organized colloidal crystals of submicron spheres have provided convenient 3D templates for the construction of macroporous photonic crystals sometimes called "inverted opals." In this approach, voids between colloidal spheres are infiltrated with a semiconductor material. Subsequent removal of the colloidal-sphere template, by either wet etching or thermal decomposition, leads to the formation of 3D ordered air cavities inside high refractive index materials.

Polymeric replicas of colloidal crystals—macroporous polymers created by the same templating approach—have successfully been demonstrated in varied applications, including use as separation media for macromolecules and DNA separation, biosensors, and "lost-wax" scaffolds for building complex colloids and colloidal crystals, as well as in optical applications. They are also promising candidates for low-k dielectric materials to reduce signal delay and cross-talk in interconnects within integrated circuits.

A variety of methods that use self-assembly can create colloidal crystals with millimeter to centimeter-sized single- or poly-crystalline domains in a time period from days to weeks. Although such methods are favorable for low volume, laboratory-scale production, scaling-up to industrial-scale mass-fabrication seems infeasible due to their tedious fabrication processes and incompatibility with the wafer-scale batch microfabrication techniques widely used by the semiconductor industry. In addition, these methods lead to non-uniform or non-controllable thickness as well as many unwanted structural defects, such as evaporation-induced cracks, which can destroy photonic band gaps and hinder the successful fabrication or development of practical devices.

These problems also impact the fabrication of macroporous polymers, as most fabrication methods for macroporous polymers involve the pre-formation of colloidal crystals as structural scaffolds.

SUMMARY OF THE INVENTION

According to one aspect of the present invention, a colloidal crystal is provided comprising one or more planes of regularly spaced spherical colloids arranged in a crystalline pattern having one or more (1,1,1) planes, the colloids having a spacing within each respective (1,1,1) plane of about 1.4 D, where D is the diameter of the colloids. According to a related aspect, a macroporous polymer is provided comprised of a polymer matrix having regularly spaced spherical voids, the voids arranged in a crystalline pattern having one or more (1,1,1) planes, the voids having a spacing within each respective (1,1,1) plane of about 1.4 D, where D is the diameter of the voids.

According to another aspect of the present invention, a method for preparing a self-assembled colloidal crystal or macroporous polymer is provided, the method including the steps of: dispersing colloidal spheres in a pohtopolymerizable material, desirably in one or more acrylate monomers; dispensing the dispersion on a substrate; spin-coating the dispersion over a surface of the substrate so as to align the spheres in hexagonally arranged layers; photo-polymerizing the spin-coated dispersion by exposure to radiation; and removing any non-polymerized portions of the spin-coated dispersion.

Additional features and various advantages of the present invention will be explained in the following detailed description. It is understood that the foregoing and following descriptions and examples are merely representative of the invention, and are intended to provide an overview for understanding the invention as claimed.

BRIEF DESCRIPTION OF THE DRAWINGS

This patent or application file contains at least one color photograph. Copies of this patent or patent application publication with color photograph(s) will be provided by the Office upon request and payment of the necessary fee.

DETAILED DESCRIPTION OF THE INVENTION

The present invention, according to one aspect, is capable of providing wafer-scale (at least as large as six-inch diameter) planar colloidal crystals through a simple and fast (as short as ten minutes) spin coating process. According to another aspect of the present invention, wafer-scale macroporous polymers can likewise be produced with the simple and fast spin coating process of the present invention.

According to yet another aspect of the present invention, planar colloidal crystals or macroporous polymers are produced comprising ordered mono layers of spheres or spherical voids, with the spheres or voids within each layer having a center-to-center distance of about 1.4 D, where D is the diameter of the spheres or voids.

According to another aspect of the present invention, the non-close-packing of spheres in (111) planes leads to low volume filling fraction of the spherical particles of the resulting colloidal crystal or low filling fraction of the corresponding voids—a filling fraction positioned between that of diamond structure (about 34%) and close-packed structures (about 74%)—at about 52%. Theoretical calculation shows that if photonic crystals have a lower filling fraction, a lower, more easily obtainable dielectric-constant contrast is sufficient to open full band gaps. Previously, the packing of microspheres in a lattice with low filling fraction by self-assembly has not been easy. The present invention achieves a desirable low filling fraction with ease and repeatability.

Figure 2:
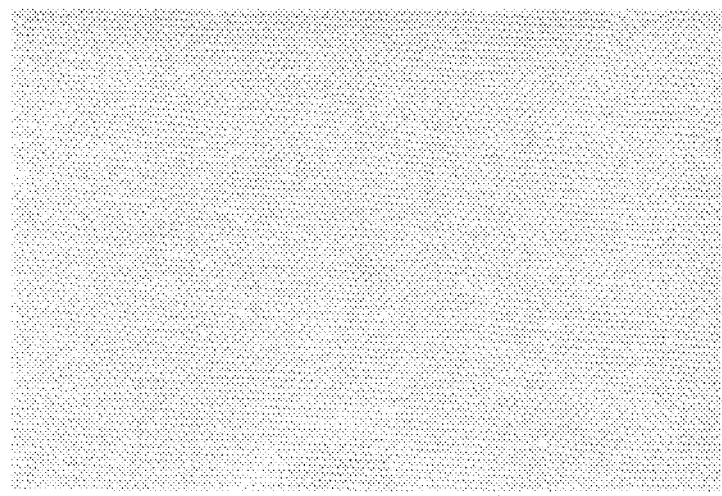
FIG. 2 is a top view scanning electron microscope (SEM) image of the embodiment shown in FIG. 1.
Figure 3:
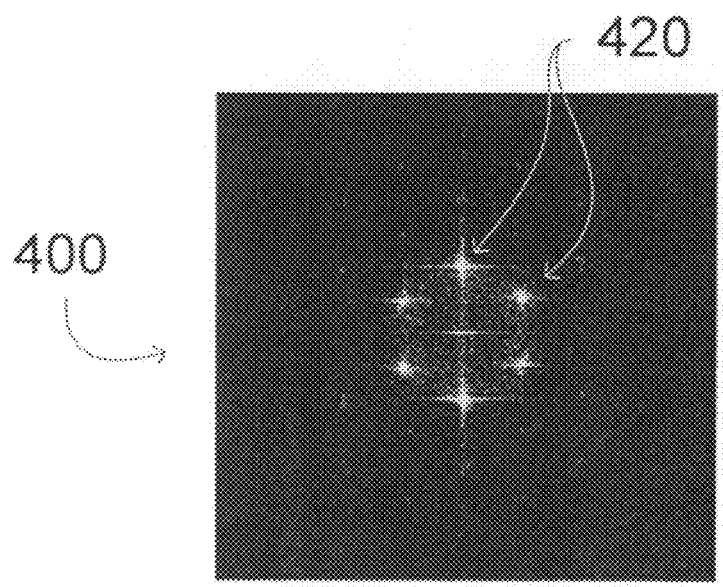
FIG. 3 is a Fourier transformed image of a 40 μm by 40 μm region in the image of FIG. 2, showing frequency components of the image of FIG. 2.
Figure 4:
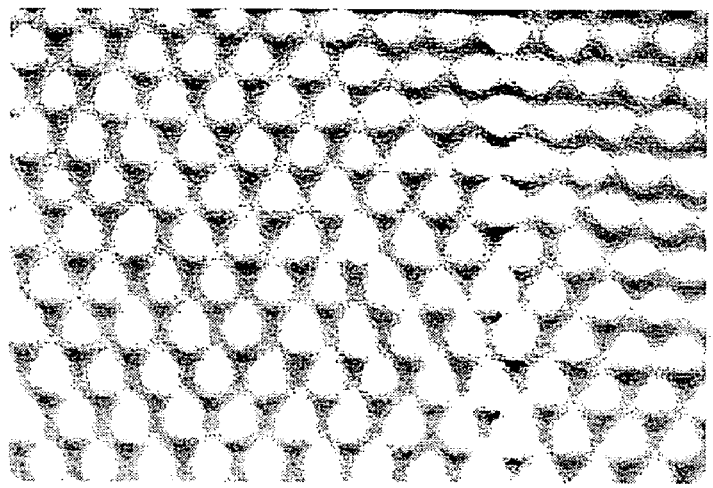
FIG. 4 is a higher magnification SEM image of the embodiment shown in FIGS. 1 and 2.

According to another aspect of the present invention, spin coating may be used with monodisperse silica colloids selected from a very a wide diameter range (from 80 nm to over 1 micron) to form 3D ordered nanocomposite films. For example, a film made from 1320 nm diameter colloids, such as that shown in FIG. 4, shows similar long-range ordering and center-to-center distance (about 1.4 D) as those of smaller spheres, such as those shown in FIGS. 1, 2, and 3, with spheres of 325 nm diameter. This wide particle diameter range achievable with the present invention is a clear advantage over previous methods in making colloidal crystals, as quick gravity sedimentation of large (greater than 400 nm diameter) silica spheres typically causes serious problems in making high-quality crystals.

Figure 5:
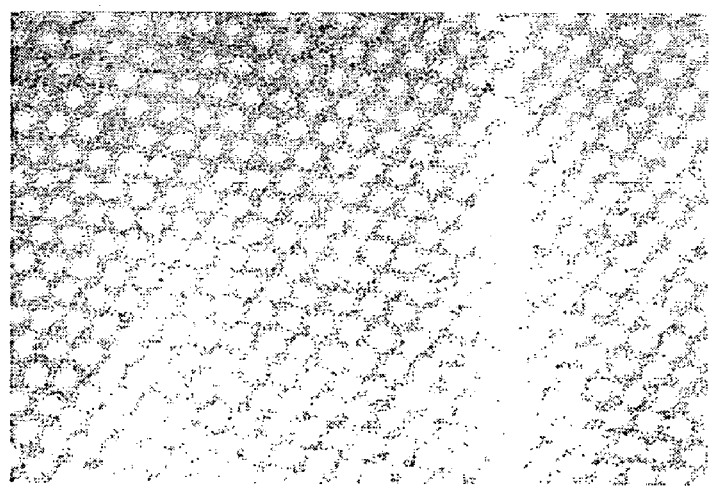
FIG. 5 is a top view SEM image of a nanocomposite film according to another embodiment of the present invention, with the film made with 1320 nm diameter colloidal spheres.

According to another aspect of the present invention, a well-ordered single domain colloidal crystal or macroporous polymer can be repeatedly and reliably formed. The ordering perpendicular to the regularly arranged top plane is apparent in the cross-sectional images of FIGS. 5 and 6. These and other side-view images of various crystallographic planes exclude the random stacking of hexagonal planes, which has been observed in some previous shear alignment experiments. Resulting structures of the present invention are oriented with their (111) planes generally parallel to the substrate. Both top and side view images (FIGS. 2,3,4,5, and 6, for example) show that embedded colloidal crystals have very low defect densities, such as stacking faults, dislocations and point vacancies. Significantly, as the spin-coating process does not involve any solvent evaporation, the whole crystal is completely free of drying-induced tension or stress cracks, which are common defects in colloidal crystals made by other methods, and are harmful to the opening of a photonic band gap and the construction of optical devices.

Figure 8:
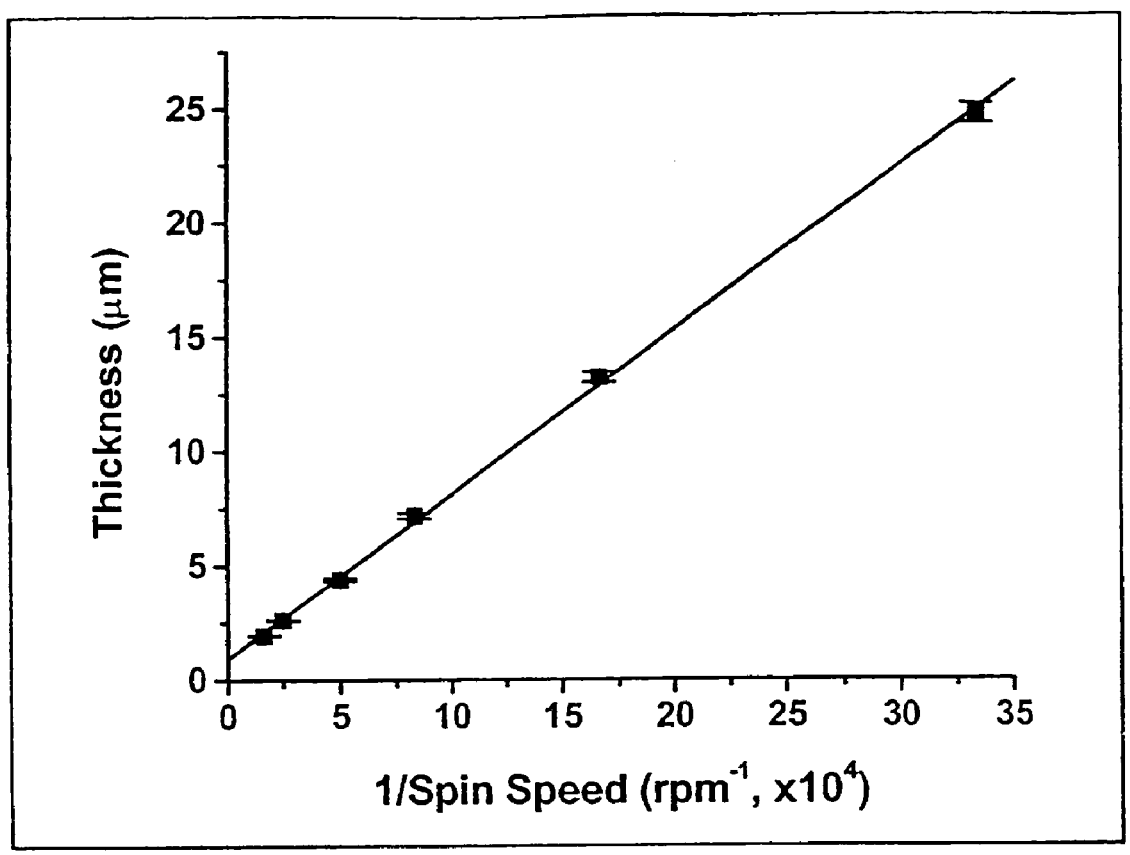
FIG. 8 is a graph of the resulting nanocomposite film thickness as a function of the inverse of the spin speed, at constant spin time of 120 seconds, using 325 nm diameter colloids.
Figure 9:
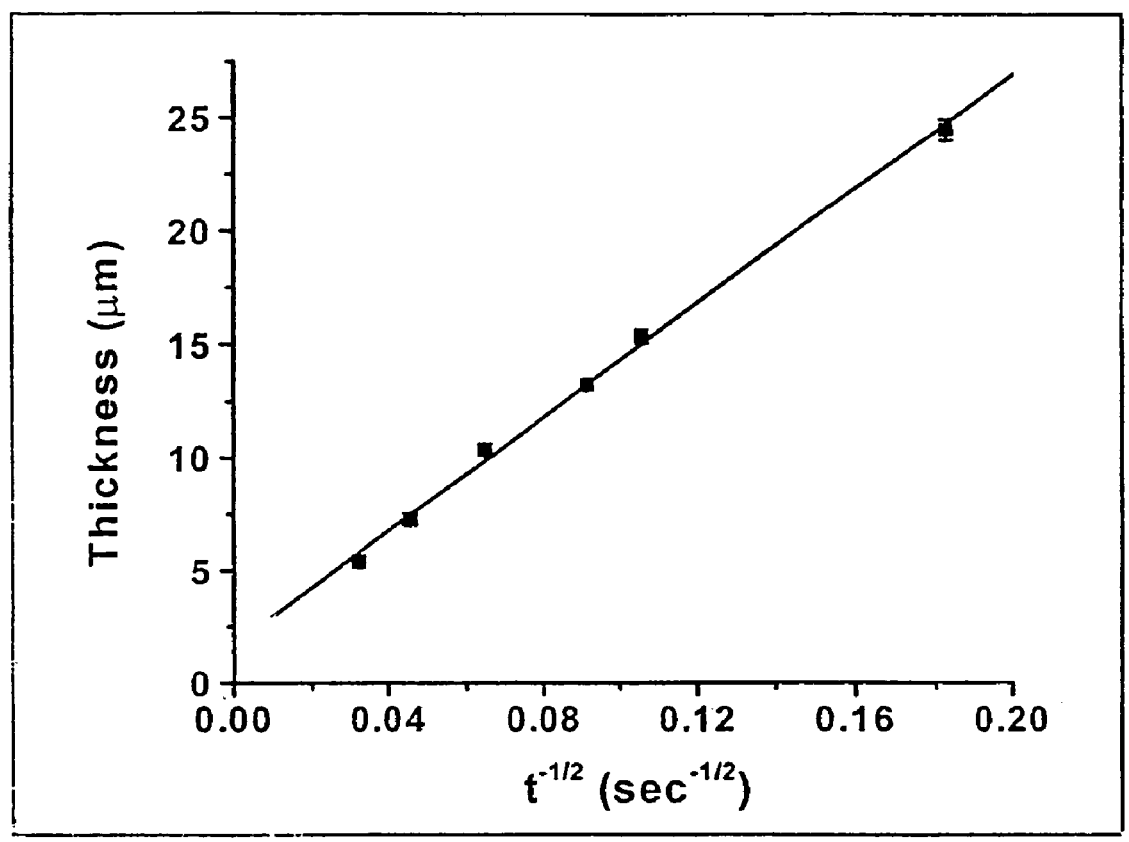
FIG. 9 is a graph of the resulting nanocomposite film thickness as a function of the inverse of the square root of spin duration (30, 90, 120, 240, 480 and 960 seconds respectively) at constant spin speed of 600 rpm using 325 nm diameter colloids.

According to another aspect of the present invention, precise control of thickness of colloidal crystal and macroporous polymer structures is achieved. Crystalline thickness is an important parameter in determining the quality of colloidal crystals. Highly uniform and tunable film thickness over a large area is much desired for the simultaneous production of multiple devices on a single substrate. The spin-coated nanocomposite films of the present invention exhibit excellent thickness uniformity with variation within a wafer (as large as six-inch diameter) of less than 2%. The film thickness can be controlled easily, by changing the spin speed and time. Thickness is inversely proportional to the final spin speed, as shown in the graph of FIG. 8, and to the square root of the final spin time, as shown in the graph of FIG. 9. This agrees well with the model of spin coating of solvent-free liquids, which predicts $$H \approx \frac{A}{\omega\sqrt{t}} \quad (1)$$

where H is the film thickness, A is a constant determined by the viscosity and density of the solution, ω and t are the final spin speed and time. FIG. 8 is a graph of the resulting nanocomposite film thickness as a function of the inverse of the spin speed, at constant spin time of 120 seconds, using 325 nm diameter colloids. FIG. 9 is a graph of the resulting nanocomposite film thickness as a function of the inverse of the square root of spin duration (30, 90, 120, 240, 480 and 960 seconds respectively) at constant spin speed of 600 rpm using 325 nm diameter colloids. From FIGS. 8 and 9, A≈97800 may be taken as an approximation in equation (1), where H is in microns, ω is in rpm and t is in seconds.

Figure 6:
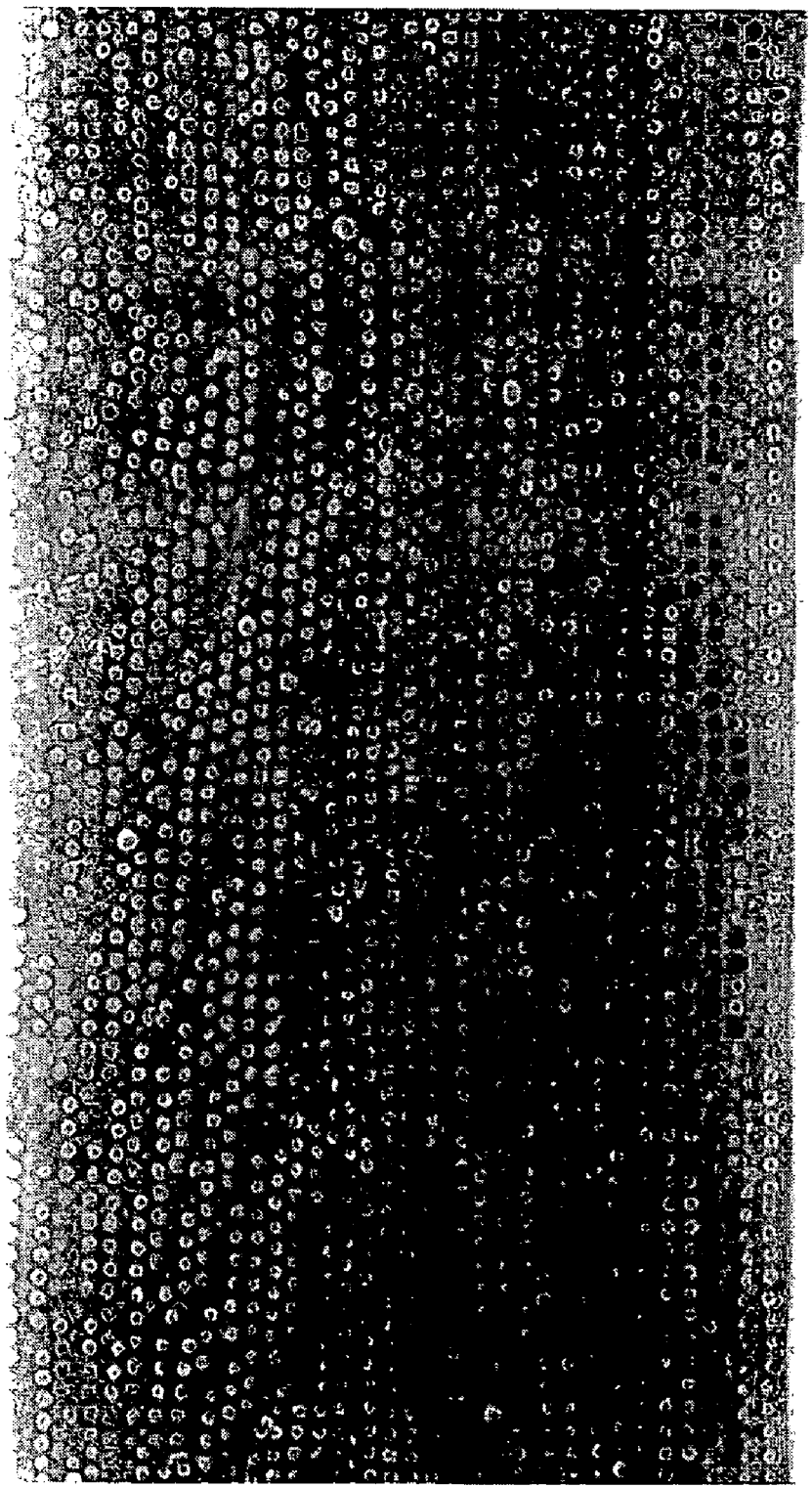
FIG. 6 is a side view image of the embodiment of FIGS. 1 and 2 showing 41 colloidal layers.
Figure 7:
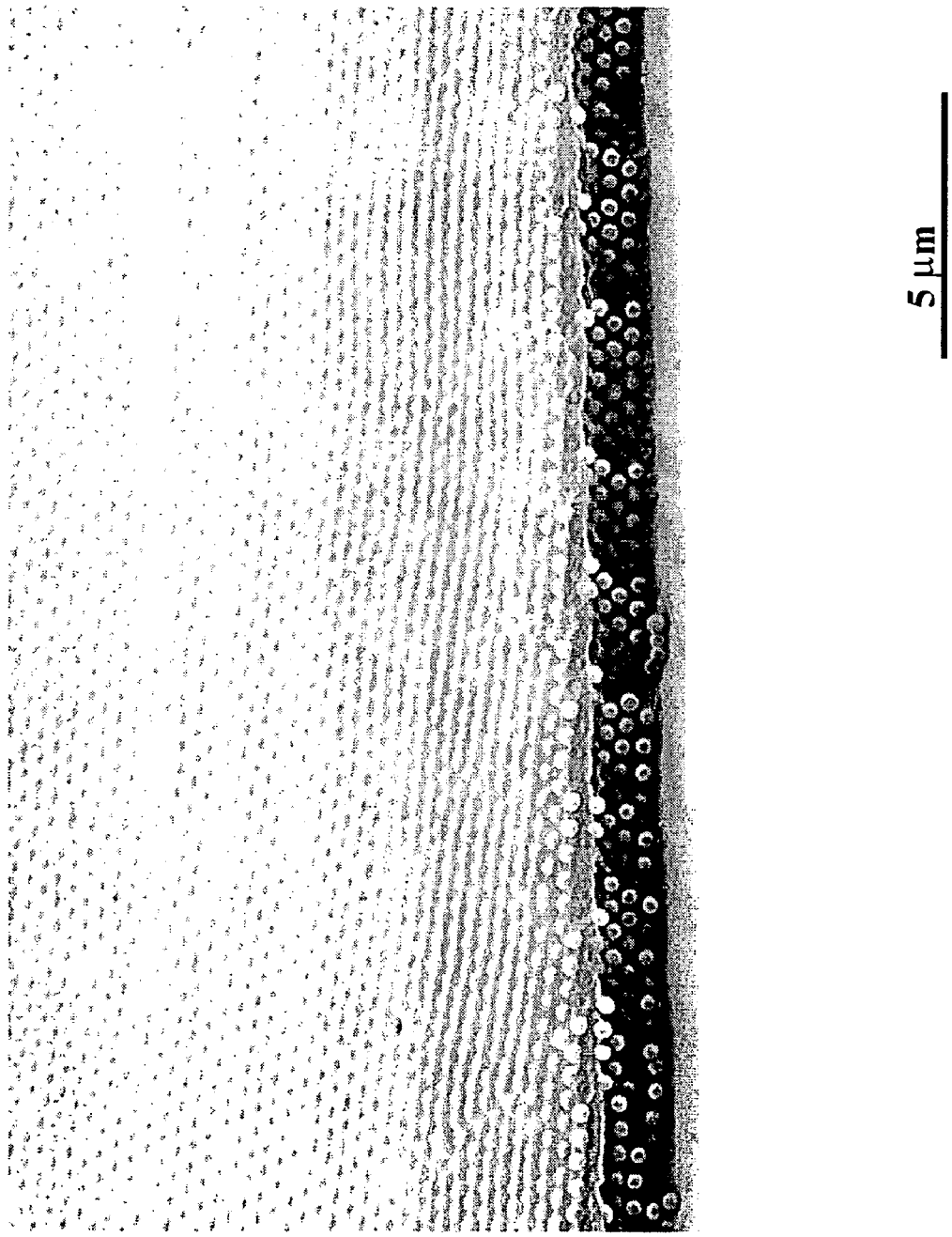
FIG. 7 is a side view image of a nanocomposite film according to yet another embodiment of the present invention, showing 5 colloidal layers comprised of 325 nm colloidal spheres.

The nanocomposite film thickness determines the number of layers of the resultant colloidal crystals and macroporous polymers, illustrated by the two crystals of 41 colloidal layers as seen in FIG. 6, and of five (5) layers, as seen in FIG. 7, made at different spin-coating conditions. Thicker films (up to 100 microns or more) can be constructed by successive spin-coating, where spheres of bottom multilayers template-induce the aligned colloidal crystallization of upper layers. Wafer-scale monolayer colloidal crystals with particle center-to-center distance of approximately 1.4 D can also be fabricated using the same spin-coating process.

The above-mentioned and other advantages are provided by a process of the present invention for forming polymer-colloid noncomposites, colloidal crystals, and macroporous polymers, and by the resulting materials or structures produced. According to an embodiment of this inventive process, concentrated solutions of silica colloids, desirably mondisperse colloids, in a viscous monomer, desirably a triacrylate monomer, are spin-coated onto a substrate. Shear-induced ordering and subsequent photopolymerization lead to the formation of two-dimensionally (in the case of monolayers) or three-dimensionally (3D) ordered colloidal crystals trapped inside a polymer matrix. The thickness of the as-synthesized colloidal crystal-polymer nanocomposite is highly uniform and can be controlled, even down to monolayer thickness, simply by changing the spin speed and time. Selective removal of the polymer matrix, such as by oxygen plasma treatment, or removal of the silica spheres, such as by wet etching, leads to the formation of large-area colloidal crystals and macroporous polymers, respectively, each with high crystalline qualities and controllable thickness. This wafer-scale process is compatible with standard semiconductor batch microfabrication, as multiple micrometer-sized patterns can be created simultaneously for potential device applications. This inventive technique provides not only an enabling method for mass fabricating photonic crystals, but a method for mass fabricating macroporous polymers for applications ranging from bio-separation to low dielectric constant (k) substrates.

Figure 10:
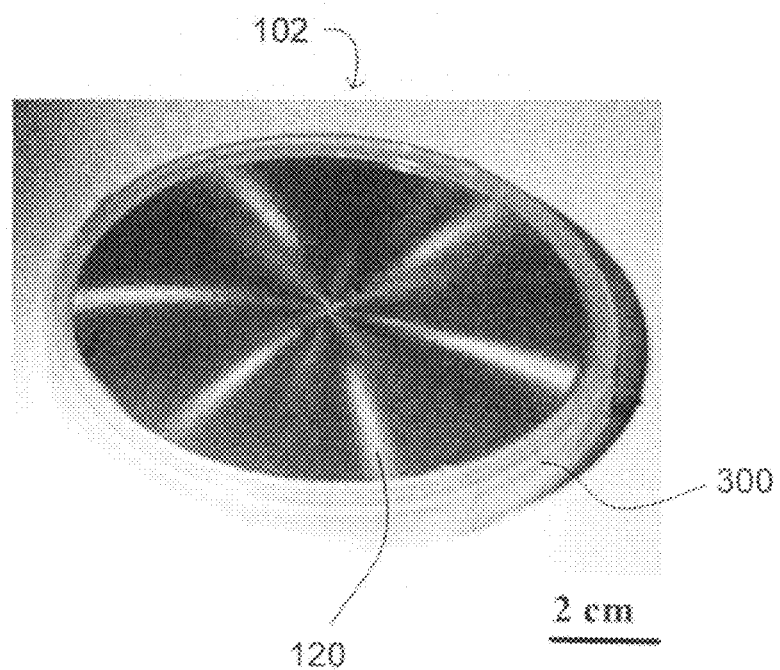
FIG. 10 is a digital camera image under white light of a resulting colloidal crystal 102, formed and supported on a wafer (not visible, shown displayed in a wafer holder 300), according to yet another embodiment of the present invention, after removal of the polymer matrix of a nanocomposite film.
Figure 11:
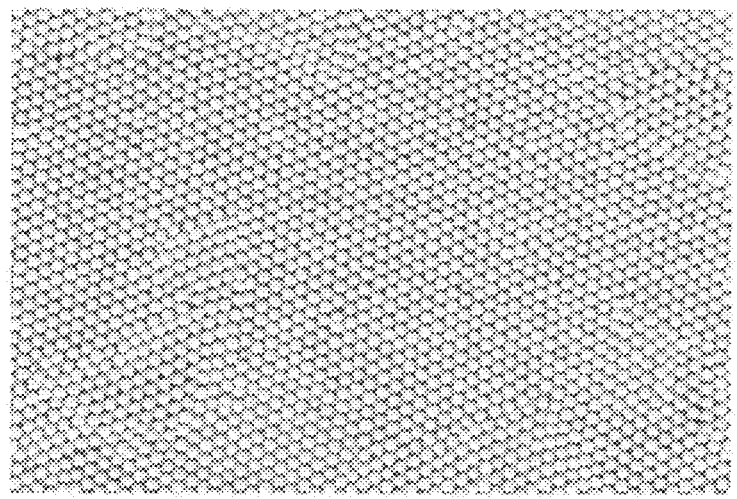
FIG. 11 is a top view SEM image of the embodiment of FIG. 10.
Figure 12:
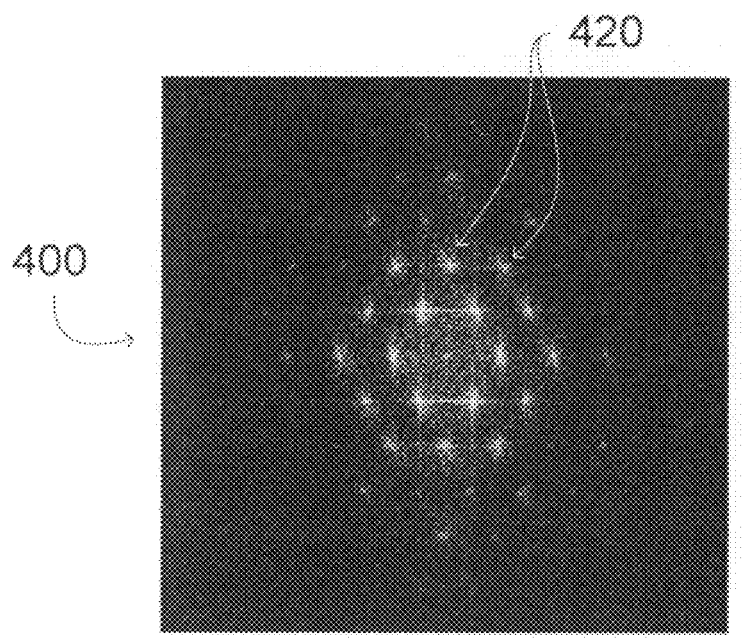
FIG. 12 is a Fourier transformed image of a region of the image of FIG. 11.
Figure 13:
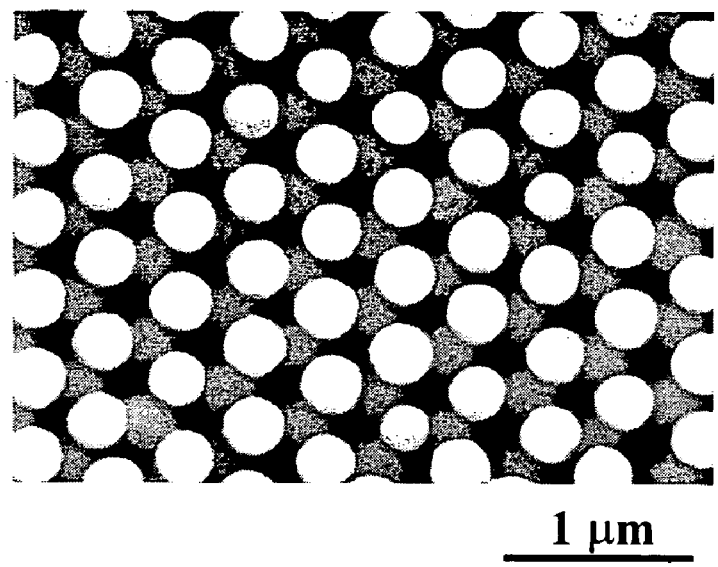
FIG. 13 is a higher magnification SEM image of the embodiment of FIGS. 9 and 10.

The spin coating method of the present invention has major merit in its ability to mass-fabricate planar colloidal crystals and macroporous polymers. Due to their substantial difference in chemical properties, ETPTA and silica can each be selectively removed without disturbing the structure of the other, resulting in the formation of colloidal crystals or macroporous polymers. Oxygen plasma etching is generally a better method than calcination in removing ETPTA polymer matrix, as it hardly affects the silica spheres and no defects, such as cracks, are introduced. The resultant planar colloidal crystal 102, shown in a digital photograph under white light in FIG. 10, exhibits stronger Bragg diffraction than the nanocomposite (FIG. 1) due to the increase in refractive index contrast when air replaces the polymer fraction. The stronger Bragg diffraction is seen by the presence of additional arms in the diffractive star 120 in FIG. 10, relative to FIG. 1. An SEM image of the (111) plane, shown in FIG. 11, and its Fourier transform image 400 shown in FIG. 12 of the (111) plane reveal the expected hexagonal arrangement of spheres with single-crystal domain and very few defects. The Fourier transform image 400 of FIG. 12 is made up of points 420 representing the frequency components of the original image. The tightly grouped, well-defined point-like groupings in the frequency-domain graph indicate a regular, well-formed array in the original image.) Similar to the original nanocomposites, silica spheres in the (111) planes keep their initial approximately 1.4 D center-to-center distance, as seen in the photograph of FIG. 13. It is also interesting to notice in FIG. 13 that spheres of the top layer only fill in the triangularly arranged crevices made by the non-touching spheres of the second layer down. Underneath, hexagonally packed (hp) layers throughout the film thickness exhibit similar non-close-packing in (111) planes and good registry between neighboring layers. This not only confirms the 3D ordering of spheres in original nanocomposite films, but also shows that silica spheres of neighboring layers are contacting, otherwise, the resultant colloidal crystals would be unstable and would collapse during oxygen plasma etching.

Figure 14:
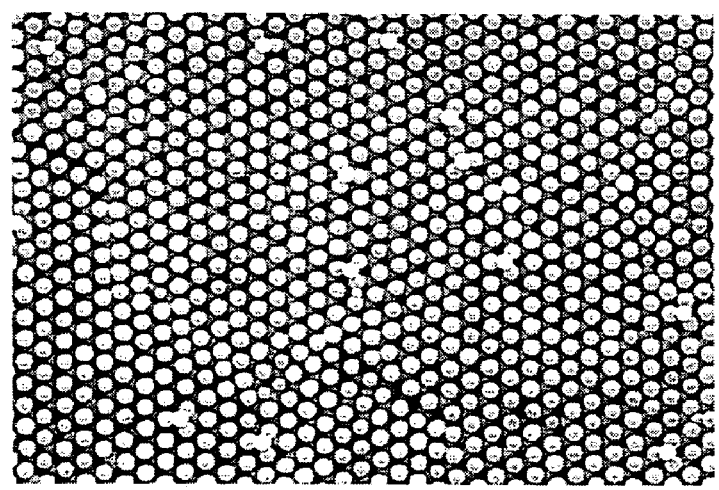
FIG. 14 is an SEM image showing yet another aspect of the present invention, the exclusive templating deposition of polystyrene spheres (320 nm, Bangs Lab) in the triangularly arranged crevices made by the top colloidal layer of the embodiment of FIGS. 9 and 10.

The non-close-packing of spheres in (111) planes leads to low particle filling fraction of approximately 52%, which is between that of diamond structure (about 34%) and close-packed structures (about 74%). Theoretical calculation shows that photonic crystals made from dielectric spheres with diamond-like low filling fraction open wider photonic band gaps, or from another perspective, a more easily obtainable dielectric constant contrast is sufficient to open full band gaps. Although the packing of microspheres in a lattice with low filling fraction by self-assembly has not been an easy in the past, the inventive technique disclosed herein provides a simple way to build low-filling-fraction colloidal crystals with high crystalline quality and controllable thickness, which are robust enough as templates for the construction of inverted photonic crystals. As a further embodiment of the methods of the present invention, this technique can be used for making binary colloidal crystals using layer-by-layer growth. Feasibility of this technique has been demonstrated by the exclusive deposition of smaller polystyrene colloids within the triangular crevices of a silica crystal, as shown in FIG. 14.

Figure 15:
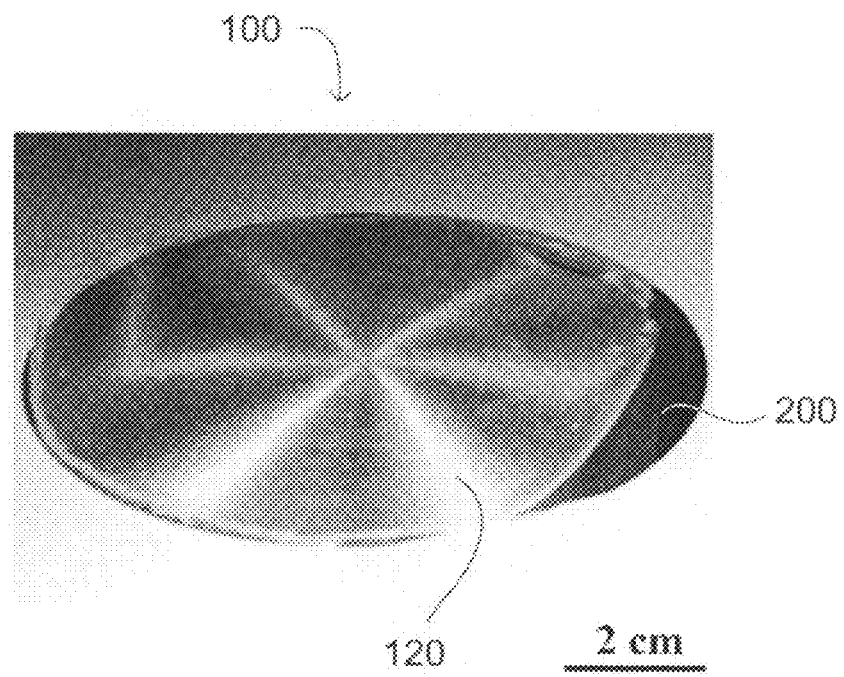
FIG. 15 is a digital image taken in white light of an embodiment of yet another aspect of the present invention, a self-standing macroporous polymer 104 after silica spheres have been removed therefrom.

Embedded silica spheres can be selectively removed, such as by hydrofluoric acid wash, to make large-area, flexible and free-standing macroporous polymers. The bright iridescent colors of such a film or polymer 104 of FIG. 15, are caused by Bragg diffraction of visible light from 3D ordered air cavities, as evidenced by the top- and side-view SEM images of FIGS. 16 and 19, and by the Fourier transform in FIG. 17 of a portion of the image of FIG. 16. As may be seen in FIG. 18, the exposed inner layers exhibit well ordered hexagonal structures, confirming ordering in (111) planes, while the registry of stacked (111) planes is evident from the cross-sectional view of FIG. 19. At higher magnification such as in FIG. 18, the interconnecting inner pores, arising from the touching sites of silica spheres in the original nanocomposites, are evident. Only six total pores lead out from each spherical cavity, because each inner silica sphere simply contacts with three upper-layer spheres and three lower-layer spheres, and not with the six neighboring spheres in the same plane. This is important for lattice stability during oxygen plasma etching, and also ensures the complete removal of silica templates in resultant macroporous polymers, which has been experimentally confirmed by the absence of elemental silicon in energy-dispersive X-ray analysis (EDAX). As in FIG. 12 discussed above, the Fourier transform image 400 of FIG. 17 is made up of points 420 representing the frequency components of the original image. The tightly grouped, well-defined point-like groupings in the frequency-domain graph again indicate a regular, well-formed array in the original image.

Without intending in anyway to limit the scope of the invention here described, the inventor presently attributes the formation of embedded colloidal crystalline structures by spin-coating to both shear induced ordering and subsequent monomer polymerization. In previous research efforts, light scattering, X-ray scattering and small-angle neutron scattering (SANS) of colloidal "hard sphere" suspensions under steady and oscillatory shear flows (in both rocking-cuvette and parallel rotating disk geometries) have revealed a sliding layer structure at large strain amplitudes, and a twined fcc structure at small ones. In the first (large strain amplitude) case, 2D hcp layers of colloids are readily formed due to the coupling of the forces of the shear field to the inter-particle forces. But the colloidal layers can freely slip past one another in the direction of flow, resulting in the formation of randomly stacked hcp layers. In the latter (small strain amplitude) case, the hcp planes move in a zigzag manner such that particles hop from one fcc twin site to the next.

In the spin-coating processes described herein, it is believed that the coupling of shear strain (arising from the velocity gradient perpendicular to the wafer surface) to the centrifugal and viscous forces, as well as the reduced inter-particle forces due to adsorbed monomers, induces the formation of sliding hp layers. The shear stress between sliding layers is believed to repel surface-absorbed monomers, thus allowing close contact of sliding planes, while the stress is believed barely to affect the particle separation due to adsorbed monomers in the (111) planes. It is believed that subsequent monomer photopolymerization plays the major role in the formation of registry between stacked hp layers. It is well known that acrylate monomers undergo volume shrinkage generally in range of 5-30% during polymerization. That shrinkage may provide sufficient driving forces for dragging neighboring hp layers with little misalignment (less than one lattice constant) into 3D ordered structure, which has minimum free energy. Indeed, in comparing confocal microscopy images of samples prior to and after photopolymerization, better crystallization has been observed for polymerized ones.

Although the underlying mechanism of the inventive method has yet to be fully understood, its simple geometry, non-volatile and viscous fluidic environment, and easily solidified structures may also provide a better method than standard PMMA/organic solvent systems for the fundamental study of shear-induced crystallization, melting and relaxation.

To make practical devices, especially for on-chip optical and optoelectronic integration, patterning of photonic crystals with micrometer regime resolution is important. The planar configuration, globally uniform thickness and wafer-supported structure of these inventive crystals allow the simultaneous construction of multiple micrometer-dimensioned patterns using standard semiconductor microfabrication techniques. For example, both proximity photolithography and reactive ion etching (RIE) have been demonstrated.

Figure 20:
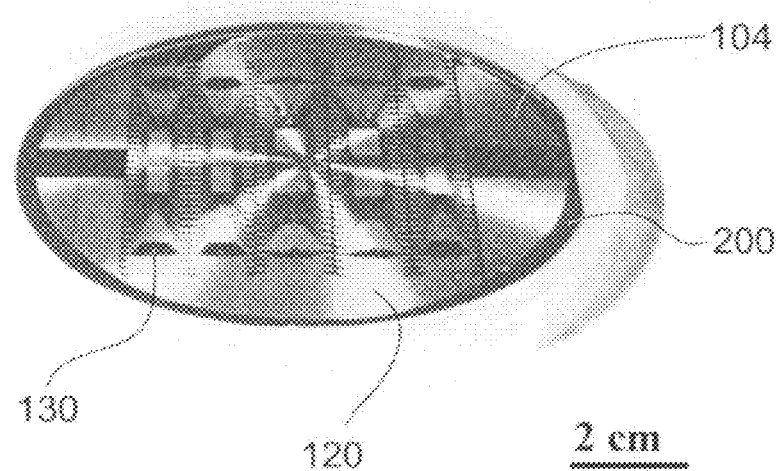
FIG. 20 is a digital image taken in white light of an embodiment of yet another aspect of the present invention, a macroporous polymer film 104 having a pattern 130 formed therein, made in this example by proximity photo-lithography.
Figure 21:
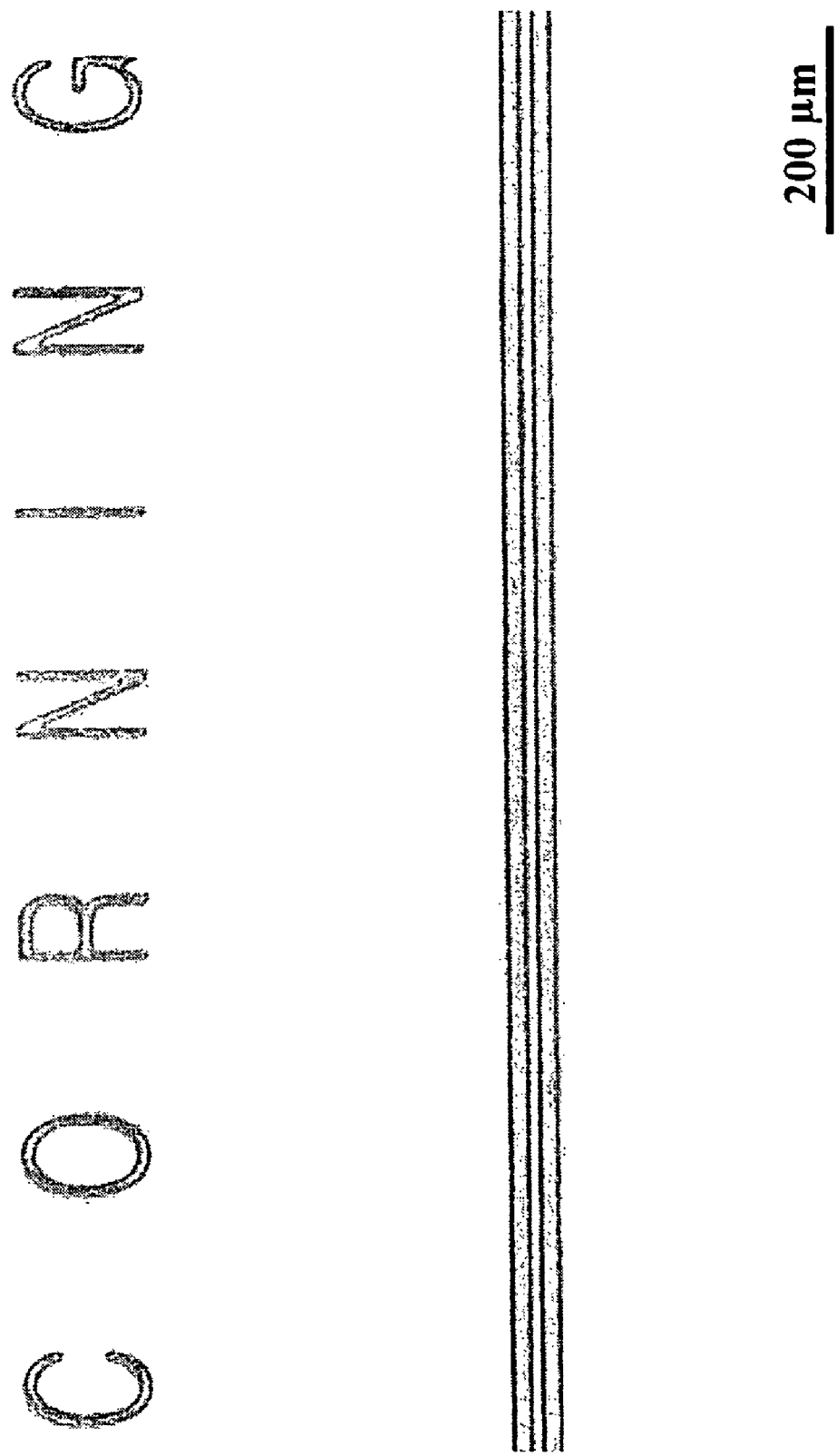
FIG. 21 is an optical microscopic image of certain of the finer features of the embodiment of FIG. 20.
Figure 22:
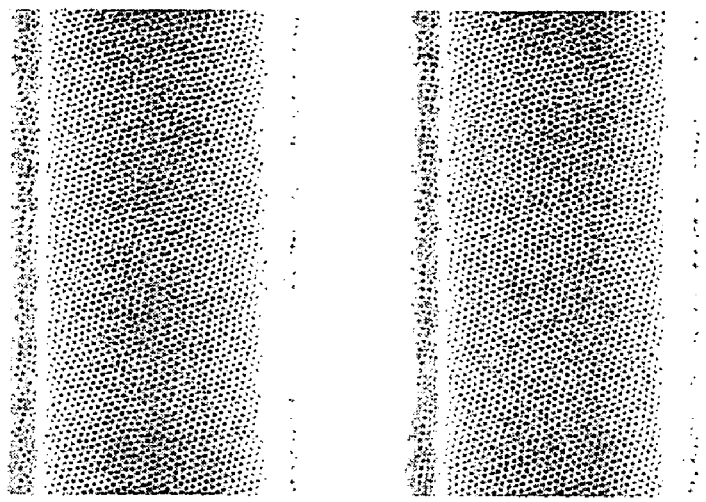
FIG. 22 is a top view SEM image of parallel lines of FIG. 21.
Figure 23:
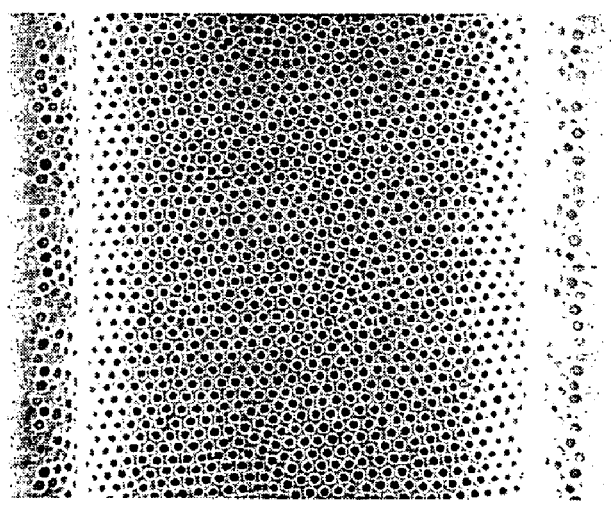
FIG. 23 is a higher magnification top view SEM image of a single line of the parallel lines of FIG. 22.
Figure 24:
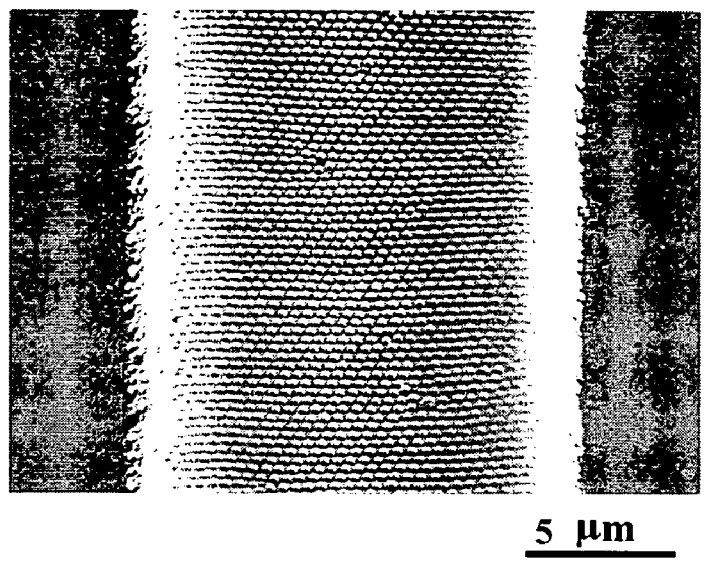
FIG. 24 is a top view SEM image showing the same view as in FIG. 23, but taken of the corresponding nanocomposite film before the removal of the spheres to form the patterned macroporous polymer of FIGS. 20-23.

A macroporous polymer film 104 resting on a wafer 200 is shown in FIG. 20, having a pattern 130 formed therein by proximity photolithography. The film 104 of FIG. 20 shows the diffraction star 120, overlayed with a dark patterned area of pattern 130, indicating the preservation of the ordered structures throughout the patterning and etching processes. To prevent the polymer from peeling off the substrate during wet etching, silicon wafers with native oxide layers are desirably primed using 3-acryloxypropyl trichlorosilane (APTCS, United Chemical Technologies), which provides both protection of the oxide layers and covalent bond linkage between the wafer and ETPTA polymer. Under an optical microscope, the well-defined features of the sample are seen as shown in the photograph of FIG. 21. FIGS. 22 and 23 show the same film viewed at higher magnification under SEM. In FIGS. 22 and 23, the regularly arranged air cavities of the sample are evident. FIG. 24 shows the patterned film noncomposite film (that is, including the silica spheres) prior to wet etching under SEM. In all these FIGS., the long-range single-crystalline domains with very low defect density are again demonstrated, making these crystals sufficient for practical microphotonic devices.

RIE can also be used to pattern polymerized nanocomposite films. Due to anisotropic etching of the RIE process, slanted surfaces of ordered spheres with well-defined angles may be formed. An example embodiment is shown under SEM in FIG. 25. The angled sidewalls can be used as reflective mirrors to couple light out of the generally planar crystal structures for optoelectronic integration.

As yet another aspect of the methods of the present invention, RIE etching and other forming of previously deposited nanocomposite layers, such as that shown in the above-described figures, can be used for the fabrication of intentional defects, such as microcavities or line defects, which are very useful in the formation of functioning photonic crystal devices. Detailed device structures can be built up using a layer-by-layer approach.

The present invention has demonstrated the formation of high-quality, large-area, 3D ordered nanocomposites, colloidal crystals and macroporous polymers with controllable thickness by a simple and fast spin-coating process. A sample as large as six inches in diameter can be created in less than ten minutes, and the crystalline quality is not compromised by the fast fabrication process, as large single-crystal domains with very few structural defects easily extend over several square centimeters. The method provides a planar configuration, a highly uniform thickness and compatibility with contemporary microfabrication, making the mass production of low-cost photonic crystal devices and other devices practical. Besides the important technological applications, the process further provides a mechanism for gathering new insights into the fundamental studies of polymer-stabilized colloidal dispersions and shear-induced crystallization and melting.

EXAMPLES

Basic Technique

Figure 1:
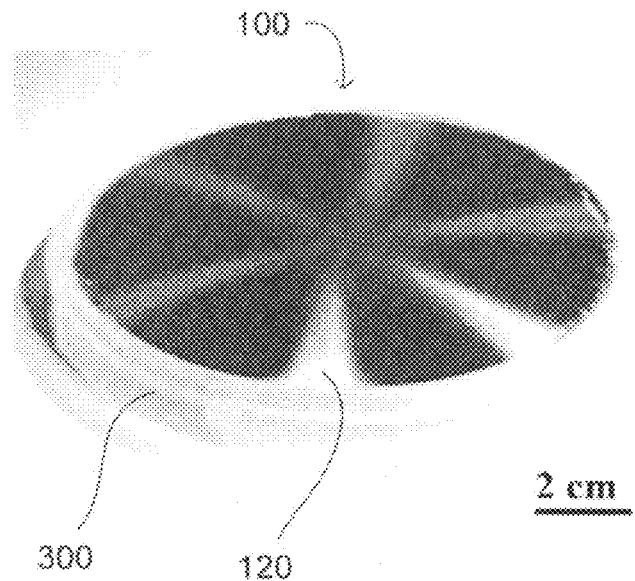
FIG. 1 is a digital camera (Canon A40) image, under white light, of a spin-coated colloidal crystal-polymer nanocomposite 100, formed and supported on a wafer (not visible, shown displayed in a wafer holder 300), according to an embodiment of the present invention, the composite comprising 325 nm diameter colloidal spheres.

Monodisperse silica microspheres were dispersed in ethoxylated trimethyloipropane triacrylate (ETPTA, SR 454, Sartomer) with 1% Darocur 1173 (Ciba-Geigy) as photoinitiator to make a final particle volume fraction of 19.8%. There was no need for extra solvent or surface modification of the silica spheres. The surprising resulting colloid/monomer dispersion stability is, on present understanding, attributed to the surface adsorption of polar triacrylate ester monomer to the silica surfaces, providing steric stabilization between colloid particles. The solution was then dispensed on a variety of wafers and spin-coated on a standard spin coater (CEE Model 100, Brewer Science). Under white light illumination, a strong monochromatic diffraction star with six arms (similar to FIG. 1) gradually replaced the iridescent polycrystalline appearance formed prior to spin coating, in about 30 seconds. The adjacent arms of the diffraction star formed exact 60° angles, indicating the formation of hexagonally packed spheres parallel to the wafer surface. As the packing assumed by the spheres during spin coating was stable and the fluid surrounding the spheres was viscous, the aligned crystals persisted after spinning ceased. The monomers were then polymerized by exposure to ultraviolet radiation. The resulting as-synthesized colloidal crystal-polymer nanocomposite film exhibits bright monochromatic diffraction, an example of which is shown in FIG. 1. When the incident angle of the illuminating white light is fixed while the wafer is rotating, the six arms of the diffraction star 120 are stationary, indicating a globally even distribution of hexagonally packed spheres.

Preparation of Colloidal Dispersions

The synthesis, purification and volume fraction determination of highly uniform silica microspheres with less than 5% diameter variation in 200-proof ethanol was performed according to P. Jiang, J. F. Bertone, K. S. Hwang, V. L. Colvin, Chem. Mat. 11, 2132 (1999). After complete centrifligation of the calculated amount of purified silica solution and discarding of the supernatant solvent, silica colloids are re-dispersed in ethoxylated trimethylolpropane triacrylate (ETPTA, M.W. 428, viscosity 60 cps, SR 454, Sartomer) using a Thermdyne Maxi Solution Mixer (type 37600). One percent (1%) by weight Darocur 1173 (2-hydroxy-2-methyl-1-phenyl-1-propanone, Ciba-Geigy) is added as photoinitiator. The final particle volume fraction is ~19.8%. After filtration through a 2 μm syringe filter (Millipore) to remove any large particles, the viscous solution is stored in an open vial overnight to allow any residual ethanol to evaporate. The concentrated solution is transparent due to refractive index matching between the silica colloid particles (n~1.43) and ETPTA (1.4689). For small silica spheres (<400 nm), the shelf life of the solution is more than six months, while for larger spheres, the precipitation of particles shortens the solution life to one to three months, but agitation can easily re-disperse the sediment. Although only ETPTA was found to stabilize silica colloids among a dozen acrylate monomers tried, surface modification of silica colloids with organosilane can greatly extend the availability of stable colloid/monomer dispersions.

Spin Coating of Colloidal Dispersions and Photopolymerization

All of the following experiments were done in a class 100 cleanroom, though this is not an absolute requirement. First, 600 μl of above silica-ETPTA solution was dispensed on a substrate. After tilting and rotating the substrate to spread the solution to achieve full wafer coverage, an iridescent polycrystalline layer with domain size of several hundred microns was formed across the wafer. The wafer was spin-coated at 200 rpm on a standard spin-coater (CEE Model 100, Brewer Science) for one minute. A Six-arm diffraction star formed in about 30 seconds. The wafer was then quickly accelerated (2000 rpm/sec) to the desired spin speed and continued to spin for the specific time needed to achieve the target thickness. Acetone was used for wafer edge bead removal. Bragg diffraction was observed even at the edges of a six-inch wafer at the highest accessible spinning speed of the spin coater, 6000 rpm, for 1000 seconds. After spin-coating, the wafer was transferred to a vacuum chamber equipped with a quartz window, and pumped down to 0.1-1.0 Torr in 30 seconds. After back-filling with nitrogen for 90 seconds, the monomer was photopolymerized using a Tamarack exposure unit operating at 23.5 mJ/cm2 for 212 seconds to obtain overall exposure dose of 5 J/cm2.

Selective Removal of ETPTA Polymer Matrix and Silica Spheres

An oxygen plasma etcher (Quartz Series, Anatech) operated at 1 torr oxygen pressure, 450 sccm oxygen flow rate and 500 W, was used to remove ETPTA polymer matrix for releasing embedded colloidal crystals. It took ~5-6 minutes for complete removal of the polymer matrix of a 30 μm thick sample. To remove silica spheres for making macroporous polymers, the same plasma etcher was used at the same conditions for only ten seconds to partially remove ETPTA polymer layer on the surface and to expose the top layer of silica spheres. This can greatly reduce the etching time of silica spheres—from overnight without plasma etching to less than ten minutes for a ~30 μm thick sample—while the ordering and porosity of the resulting macroporous polymers are not affected. A 2% hydrofluoric acid aqueous solution was used to remove the silica template.

Proximity Photolithography and Reactive Ion Etch (RIE)

For proximity photolithography patterning, the spin-coated wet colloidal crystal-monomer film was covered with a photomask with pieces of tungsten wires (GoodFellow, Cambridge) used as spacers for separating the photomask and the monomer-coated wafer. Tungsten wires of different diameters were chosen to make the proximity gap as small as possible, typically less than five microns. After exposure to UV radiation at 23.5 mJ/cm2 for four seconds, the un-exposed monomer and silica colloids were removed by an acetone rinse. The wafer was then flood-exposed to a dosage level of 5 J/cm2 for complete polymerization.

For RIE patterning, 300 nm thick aluminum (DC magnetron sputter-deposited using Perkin-Elmer 2400) was photolithographically patterned using conventional resist and wet etching to open etching windows in the aluminum layer. An oxygen reactive ion etcher (PlasmaTherm 790, Unaxis) operated at 30 mtorr oxygen pressure, 50 sccm flow rate and 500 W power, was then used to remove ETPTA underneath the etching windows. It took ~5 minutes for complete removal of uncovered ETPTA of ~30 microns thick. The exposed silica spheres were then removed by a 1% hydrofluoric acid rinse for 40 seconds.

Example 1

In accordance with the foregoing, four-inch silicon wafer was spin-coated with a colloidal suspension of 325 nm diameter spheres at 600 rpm for 120 seconds. The monomer was the polymerized as described above. FIGS. 1, 2, 4, and 6 show the resulting 41-layer nanocomposite film. A Nikon Optiphot 200C light microscope in confocal mode was used to optically section the nanocomposite film shown in FIG. 1. Each layer of the film exhibited hexagonal long-range ordering of spheres. A scanning electron microscope (SEM) image, FIG. 2, and its Fourier transform, FIG. 3, demonstrate the highly ordered structures with hexagonal packing on the film surface. At higher magnification, another interesting feature is evident, i.e. the spheres of the top layer are not touching each other, but exhibit center-to-center distance around 1.41 D (FIG. 3), where D is the diameter of colloids. This is possibly caused by spatial repulsion between colloidal spheres, arising from the adsorbed monomer layers on silica surfaces. As in FIGS. 12 and 17 discussed above, the Fourier transform image 400 of FIG. 3 is made up of points 420 representing the frequency components of the original image. The tightly grouped, well-defined point-like groupings in the frequency-domain graph again indicate a regular, well-formed array in the original image.

Example 2

A nanocomposite film was produced in accordance with the foregoing by spin-coating a dispersion of 1320 nm diameter spheres at 600 rpm for 120 seconds. The resulting nanocomposite film is shown in the SEM image of FIG. 5.

Example 3

A nanocomposite film was produced in accordance with the foregoing by spin-coating a dispersion of 325 nm diameter spheres at 6000 rpm for 170 seconds. A side view image of the resulting 5-(five-) layer nanocomposite film is shown in FIG. 7. The same process, after removal of the polymer material, produced the 5-layer colloidal crystal on a 4-inch silicon wafer shown in FIGS. 10, 11, and 13.

Example 4

A five-layer colloidal crystal as produced in Example 3 above was further processed by depositing polystyrene particles thereon, by spin-coating 1 ml of an aqueous solution of polystyrene spheres of 0.01% volume fraction at 600 rpm for 60 seconds. As before noted, the resulting deposition of polystyrene, shown in FIG. 14, shows the exclusive templating of polystyrene spheres in the triangularly arranged crevices made by the top colloidal layer of the crystal of Example 3.

Example 5

Figure 16:
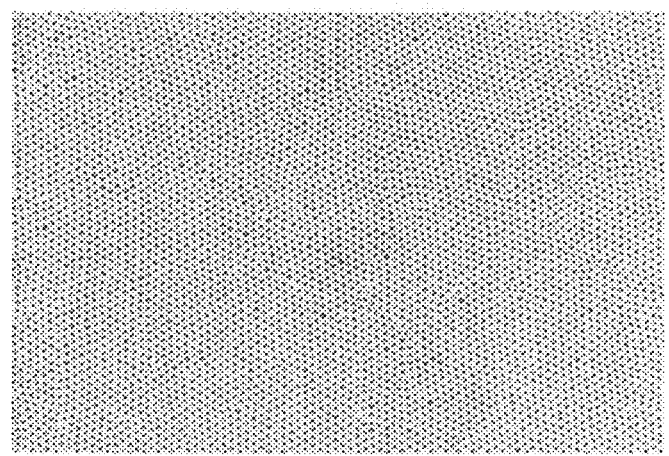
FIG. 16 is a top view SEM image of the macroporous polymer of FIG. 15.
Figure 17:
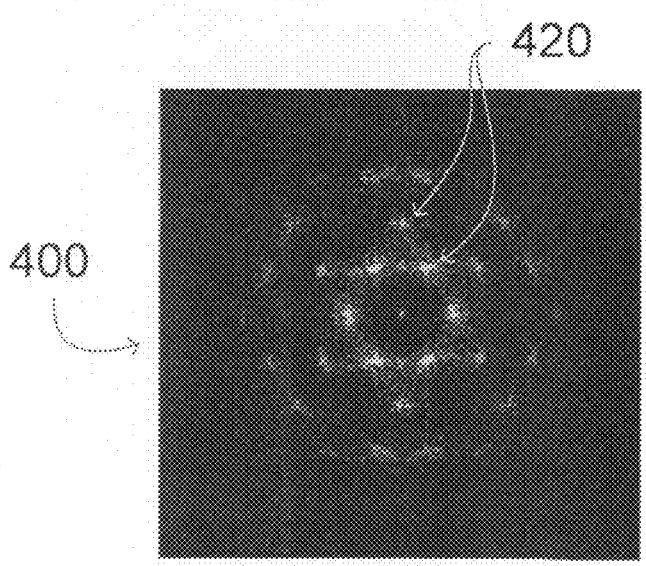
FIG. 17 is a Fourier transformed image of a region of the image of FIG. 16.
Figure 18:
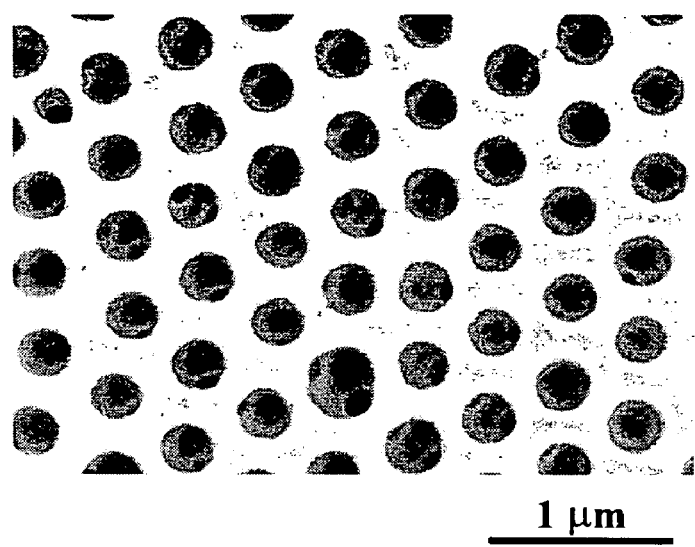
FIG. 18 is a higher magnification SEM image of the macroporous polymer of FIGS. 15 and 16, showing interconnecting inner pores.
Figure 19:
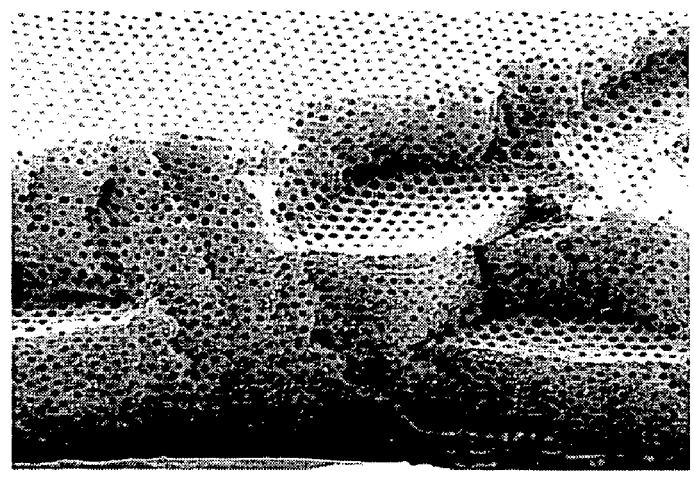
FIG. 19 is a cross-sectional image of the embodiment shown in FIGS. 15, 16, and 18.

A nanocomposite film was produced in accordance with the foregoing by spin-coating a dispersion of 325 nm diameter spheres at 600 rpm for 270 seconds. The silica spheres were then removed by wet etching as described above. The resulting self-standing macroporous polymer 104 is shown in FIG. 15, placed on a 4-inch silicon wafer 200 and illuminated with white light. (The wafer is present only to provide a dark background and a size reference.) The diffractive star 120 again shows the presence of Bragg diffraction. A top-view SEM image is shown in FIG. 16, with its Fourier transform in FIG. 17. A more magnified SEM image, showing the interconnecting inner pores, is shown in FIG. 18. A cross-sectional view is shown in FIG. 19.

Example 6

A dispersion of 325 nm diameter silica spheres was spin-coated onto a wafer at 600 rpm for 60 seconds, followed by an exposure by means of proximity photolithography. After removal of the non-polymerized material, the silica spheres where removed by wet etching. The resulting 4-inch patterned macroporous polymer layer is shown in FIG. 20, with an optical microscope image thereof in FIG. 21, and SEM images of increasing magnification in FIGS. 22 and 23. FIG. 24 shows an SEM image of the film after exposure and removal of the non-polymerized material, but before removal of the silica spheres. In order to form a lithographically patterned colloidal crystal, the polymer material in FIG. 24 can be removed instead of the spheres.

Example 7

Figure 25:
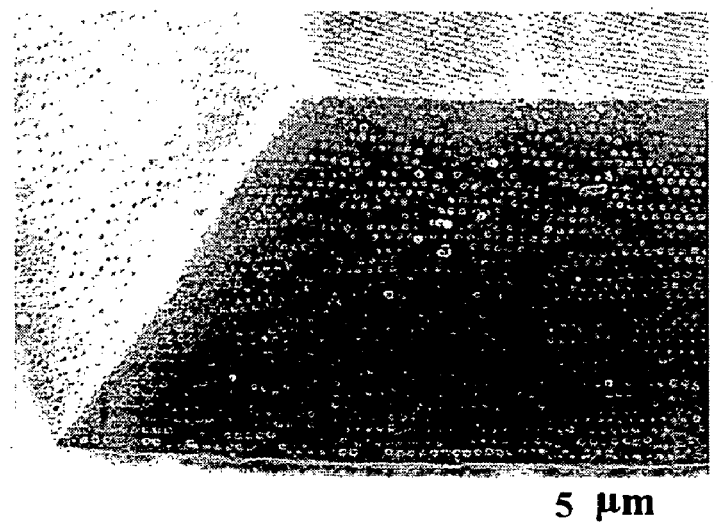
FIG. 25 is a side view SEM image of a patterned nanocomposite film, made in this example by isotropic reactive ion etching.

A nanocomposite film was produced in accordance with the foregoing by spin-coating a dispersion of 325 nm diameter spheres at 600 rpm for 120 seconds. The resulting polymer/colloidal crystal nanocomposite film was then patterned by anisotropic reactive ion etching. A side view SEM image of the resulting formation is shown in FIG. 25.

The present invention has been described generally and in detail by way of examples and figures. Persons skilled in the art, however, will understand that the invention is not limited necessarily to the embodiments specifically disclosed, but that modifications and variations can be made without departing from the spirit of the invention. Therefore, unless changes otherwise depart of the scope of the invention as defined by the following claims, they should be construed as being included herein.

What is claimed is:

1. A colloidal crystal comprised of stacked spherical colloids, the colloids having a volume filling fraction within said crystal of about 50%.

2. A colloidal crystal comprised of stacked spherical colloids, the colloids having a volume filling fraction within said crystal of about 52%.

3. A self-assembled colloidal crystal comprised of stacked spherical colloids, the colloids having a volume filling fraction within said crystal of about 50%.

4. A self-assembled colloidal crystal comprised of stacked spherical colloids, the colloids having a volume filling fraction within said crystal of about 52%.

* * * * *